United States Patent
Nilsson et al.

(10) Patent No.: US 11,587,025 B2
(45) Date of Patent: Feb. 21, 2023

(54) PROCEDURE TRAY MANAGEMENT

(71) Applicant: Mölnlycke Health Care AB, Gothenburg (SE)

(72) Inventors: Sven Nilsson, Vallda (SE); Marie Berggren, Västra Frölunda (SE); Anna Dahlberg, Västra Frölunda (SE); Björn Carlzon, Västra Frölunda (SE)

(73) Assignee: MÖLNLYCKE HEALTH CARE AB, Gothenburg (SE)

( * ) Notice: Subject to any disclaimer, the term of this patent is extended or adjusted under 35 U.S.C. 154(b) by 75 days.

(21) Appl. No.: 16/311,249

(22) PCT Filed: Jun. 20, 2017

(86) PCT No.: PCT/EP2017/065068
§ 371 (c)(1),
(2) Date: Dec. 19, 2018

(87) PCT Pub. No.: WO2017/220566
PCT Pub. Date: Dec. 28, 2017

(65) Prior Publication Data
US 2019/0237188 A1   Aug. 1, 2019

(30) Foreign Application Priority Data
Jun. 21, 2016  (EP) .................................... 16175554

(51) Int. Cl.
*G06Q 10/08* (2012.01)
*G16H 40/20* (2018.01)
(Continued)

(52) U.S. Cl.
CPC ........... *G06Q 10/087* (2013.01); *G06Q 10/10* (2013.01); *G16H 20/40* (2018.01); *G16H 40/20* (2018.01); *G16H 40/63* (2018.01); *G16H 40/67* (2018.01)

(58) Field of Classification Search
CPC .............................. G16H 40/20; G16Q 10/087
See application file for complete search history.

(56) References Cited

U.S. PATENT DOCUMENTS

| | | | | |
|---|---|---|---|---|
| 2001/0016821 A1* | 8/2001 | DeBusk | ................. | G06Q 10/08 705/2 |
| 2002/0082866 A1* | 6/2002 | Ladouceur | ............. | G06Q 40/04 705/2 |

(Continued)

FOREIGN PATENT DOCUMENTS

| | | | | |
|---|---|---|---|---|
| JP | 3155016 B2 * | 4/2001 | .......... | G06F 19/322 |
| WO | WO-98/49645 A1 | 11/1998 | | |
| WO | WO-2013/036496 A1 | 3/2013 | | |

OTHER PUBLICATIONS

International Search Report and Written Opinion dated Sep. 15, 2017 by the International Searching Authority for Patent Application No. PCT/EP2017/065068, which was filed on Jun. 20, 2017 and published as WO 2017/220566 on Dec. 28, 2017 (Inventor—Nilsson et al.; Applicant—Mölnlycke Health Care AB) (16 pages).

*Primary Examiner* — Sheetal R Paulson
(74) *Attorney, Agent, or Firm* — Ballard Spahr LLP

(57) ABSTRACT

A computer implemented method for procedure tray management, comprising storing in a database a set of procedure tray types, displaying, on a user interface, a list of procedure tray types, and displaying, in response to a user input, a list of items included in a selected procedure tray type. The method further includes automatically determining a recommended modification to the selected procedure tray type by identifying recommended item additions as items which are included in a template associated with the selected procedure tray type and not included in the selected procedure tray and electronically communicating the proposed modified procedure tray type to at least some users associated with the selected procedure tray. In response to a confirmation from (Continued)

at least one user the selected procedure tray type is updated in the database.

20 Claims, 8 Drawing Sheets

(51) Int. Cl.
*G16H 40/63* (2018.01)
*G16H 20/40* (2018.01)
*G16H 40/67* (2018.01)
*G06Q 10/10* (2012.01)
*G06Q 10/087* (2023.01)

(56) References Cited

U.S. PATENT DOCUMENTS

| | | | |
|---|---|---|---|
| 2012/0041770 A1* | 2/2012 | Philippe | G16H 40/20 |
| | | | 705/2 |
| 2012/0311781 A1 | 12/2012 | Purdy et al. | |
| 2013/0110667 A1 | 5/2013 | Debusk et al. | |
| 2014/0006943 A1* | 1/2014 | Robbins | H04L 67/025 |
| | | | 715/273 |
| 2016/0117062 A1 | 4/2016 | Hussam et al. | |
| 2016/0367268 A1* | 12/2016 | Martin | A61B 90/94 |
| 2017/0098049 A1* | 4/2017 | Sweeney | A61B 90/361 |

* cited by examiner

Fig. 5

| Reviewers | | Add comment |
|---|---|---|
| Search and add reviewers here | | New changes to review |

Mandatory User, Mandatory User

◆ Esther XXXXX, Group Product Manager
  ProcedurePak

◆ Tolgay XXXXX, Developer

Cancel    Send

*Fig. 7*

PROCEDURE TRAY MANAGEMENT

CROSS-REFERENCE TO RELATED APPLICATIONS

This application is a U.S. National Phase Application of International Application No. PCT/EP2017/065068, filed Jun. 20, 2017, which claims priority to European Application No. 16175554.1, filed Jun. 21, 2016, each of which are hereby incorporated by reference in their entirety.

FIELD OF THE INVENTION

The present invention relates to management of procedure trays.

BACKGROUND OF THE INVENTION

Various items (e.g. tools and other equipment) used in a surgical procedure are typically individually packed in a sterile package. However, in an effort to use less package material, and thereby reduce cost and environmental impact, and also save time during the procedure, composite packages including a plurality of different items have been introduced on the market. Such composite packages, sometimes referred to as "procedure trays" or "surgical trays", are typically designed for a specific surgical procedure, and ideally include all single use items required for that procedure.

Each procedure tray may include a large number of single use items, e.g. in the order of tens of items up to a hundred items or more, ranging from protective gowns, drapes and sutures to laparoscopic and orthopedic instruments. The procedure trays not only provide an efficient packaging of the items expected to be required during the procedure, but may also serve to arrange those items in a manner appropriate for the procedure, e.g. based on the order in which the items are expected to be used. The packs may also be packed in a manner providing a well balanced pack, and also a space efficient storage of the packs.

Each hospital (or group of hospitals) will typically have their "own" set of procedure trays, including the items used when performing the procedure at that specific hospital. This creates a large number of different packs, which all need to be separately handled in the purchasing process. This places a significant logistic burden on the suppliers of such trays, in terms of assembly, storage and distribution of the trays.

Despite the fact that the procedure tray is intended to include all single use items required for a procedure, additional items which are individually packaged, may still be used during the procedure. There may be various reasons for this, including different preferences of individual surgeons or nurses, minor deviations from the planned surgical procedure, etc. As each use of an individually packed item increases cost and amount of waste, there is a desire to minimize such use, and as far as possible optimize the procedure trays.

However, the large number of different trays makes it extremely difficult to implement and oversee such optimization. Optimization is further complicated by the fact that actual users of the tray (surgeons and operating room nurses) typically do not have authority to directly order new trays, but this is typically handled by designated procurement officers, at the hospital or group of hospitals. The acts of identifying suitable modifications of various packs, verifying compatibility with existing procurement arrangements and eventually ordering and supplying a modified tray, therefore becomes a very complex largely manual process, involving several people at different organizational levels and physical locations. Also, hospital efficiency and especially efficiency in the operating theater is a driver for optimizing surgical tray offers and there is a need to provide a wide variety of components are ideally possible to add to the surgical tray.

One example of customer management of procedure trays is provided by document US2013/0110667.

However, in order to achieve more optimized procedure tray, matching the needs of the surgical teams in different hospitals, and to thereby even further reduce the cost and environmental impact of excess packaging, a more efficient and automated management of procedure trays is desired.

General Disclosure of the Invention

It is an object of the present invention to provide a more efficient and automated management of procedure trays solving or at least alleviating the problems discussed above.

According to a first aspect, this and other objects are achieved by a computer implemented method for procedure tray management, comprising storing, in a database on a network attached server, a set of procedure tray types, each including a list of items to be included in a procedure tray intended to be used in a specific surgical procedure, each procedure tray type being associated with a set of users, storing, in the database, a template, including a list of items required to perform the surgical procedure associated with a particular procedure tray type, providing a database application software configured to communicate with the database, the database application software including a user interface, displaying, on the user interface, a list of procedure tray types associated with a current user of the user interface, receiving a user input indicating a selected one of the procedure tray types in the list, in response to the user input, displaying, on the user interface, the list of items included in the selected procedure tray type, allowing the current user to use the interface to indicate modifications of the list of items, automatically determining a recommended modification to the selected procedure tray type by identifying recommended item additions as items which are included in the template associated with the selected procedure tray type and not included in the selected procedure tray type, presenting the recommended modification to the current user as a proposed modified procedure tray type including a modified list of items, electronically communicating the proposed modified procedure tray type to at least some users in the set of users associated with the selected procedure tray, receiving a confirmation from at least one user in the set, and in response to the confirmation, updating the selected procedure tray type in the database.

According to a second aspect, this and other objects are achieved by a computer implemented procedure tray management system, comprising a database on a network attached server storing a set of procedure tray types, each including a list of items to be included in a procedure tray intended to be used in a specific surgical procedure, each procedure tray type being associated with a set of users, and a template, including a list of items required to perform the surgical procedure associated with a particular procedure tray type, at least one network attached workstation, a database application software including a server module installed on the network attached server and a client module installed on the network attached workstation, the server module configured to communicate with the database and with the client module, a user interface provided by the client module of the database application software, the user interface being configured to display a list of procedure tray types associated with a current user of the user interface, receive a user input indicating a selected one of the procedure tray types in the list, in response to the user input, display the list of items included in the selected procedure tray type, allow the current user to indicate modifications of the list of items, presenting a recommended modification of the selected procedure tray type to the current user as a proposed modified procedure tray type including a modified list of items resulting from the modifications.

The server module is further configured to automatically determine the recommended modification by identifying recommended item additions as items which are included in the template associated with the selected procedure tray type and not included in the selected procedure tray type.

The client module is further configured to electronically communicate the proposed modified procedure tray type to at least some users in the set of users associated with the selected procedure tray, and receive a confirmation from at least one user in the set.

The server module is further configured to update, in response to the confirmation, the selected procedure tray type in the database.

According to the invention, definitions of different procedure trays are stored in a database, making it possible to provide a user with an automated interface to all procedure trays which the user is associated with. The interface allows the user to make proposed changes to a specific tray, and then electronically communicates with other users associated with the specific tray in order to confirm the proposed change.

The invention is based on the realization that the functionality of an interface can be made more effective by storing information related to the procedure trays in a specific format in a network accessible database. The invention is further based on a unique functionality of the interface, enabling a more efficient tray modification process.

According to the invention, a proposed modification to a particular procedure tray type is automatically proposed and presented to the current user. This even further improves the efficiency of the procedure tray management. Again, it is the novel storage of procedure tray information, and the user interface allowing all associated users of a procedure tray type to access this procedure tray type, that enables an automated process for making and confirming proposed modifications.

With a method and system according to the present invention, an improved overview is provided also of a very large number of unique procedure tray types, down to individual components. Traditionally, it has been increasingly difficult to keep track of all varieties of procedure trays, leading to a situation where some trays are "black holes".

Another advantage is increased traceability, as the present invention makes it possible to immediately determine who suggested and/or approved a particular modification of a procedure tray type.

The proposed modification may relate to the currently selected procedure tray, and may then be displayed on the user interface to the current user in response to indication of the selected user tray. In other words, the user will determine which procedure tray he/she wishes to work with, and only then are proposals presented by the system.

Alternatively, or in combination, the proposed modification may be communicated to all users associated with the particular procedure tray type, independently on any indication of this particular procedure tray. The process of proposing modification can in this case be considered as a parallel background process, operating independently of the current user indication. In fact, in this case, the user indication of a specific procedure tray may be prompted by a proposed modification made by the system.

Further, prices and aggregated purchasing volumes of individual items for a specific purchasing entity (e.g. a hospital or group of hospitals) to which the current user belongs may be stored in the database. Then at least one replaceable item, which has an available substitute item having technical properties equivalent to the replaceable item, may be identified in the particular procedure tray, and prices and purchase volumes of all such identified items and their respective substitute items may be compared, and item substitutions which are beneficial to the purchasing entity may be proposed. Although this particular embodiment has an underlying business purpose, its implementation is still clearly technical. In particular, the expression "replaceable item" relates to a technically equivalent item, indicating that the selection of item substitutions is based on technical factors.

For a proposed modification, an estimated set-up time saving may be determined and presented to the current user. Also, estimated waste and/or cost reductions may be determined and presented to the current user. The determination and presentation of set-up time, cost and waste consequences of a proposed modification may serve to promote procedure tray modifications that lead to faster set-up time for procedures and less waste.

According to one embodiment, the method may include defining a set of different user roles, including at least purchaser and clinical practitioner. The functionality of the user interface and the choice of information presented to the user may then be adapted based on the role of the current user. For example, estimated set-up time savings or cost savings may be presented only to users for whom it is beneficial.

According to a further embodiment, the database stores aggregated purchasing volumes of individual items for a specific business unit to which the current user belongs. The database may then be queried to find aggregated purchasing volumes of all items in the procedure tray types associated with the current user, and the resulting purchasing volumes may be presented on the user interface.

Such a process provides an efficient way to collect and present continuously updated information about purchasing volumes, which may be highly relevant for some users.

A procedure tray managed by a method of the present invention may typically include at least protective gowns, drapes, and gloves. Such items can be expected to be needed at any surgical procedure, and therefore form the basis of most surgical trays.

BRIEF DESCRIPTION OF THE DRAWINGS

The present invention will be described in more detail with reference to the appended drawings, showing currently preferred embodiments of the invention.

FIGS. 5-9 are screen shots of a user interface according to an embodiment of the present invention.

DETAILED DESCRIPTION OF PREFERRED EMBODIMENTS

Figure 1:
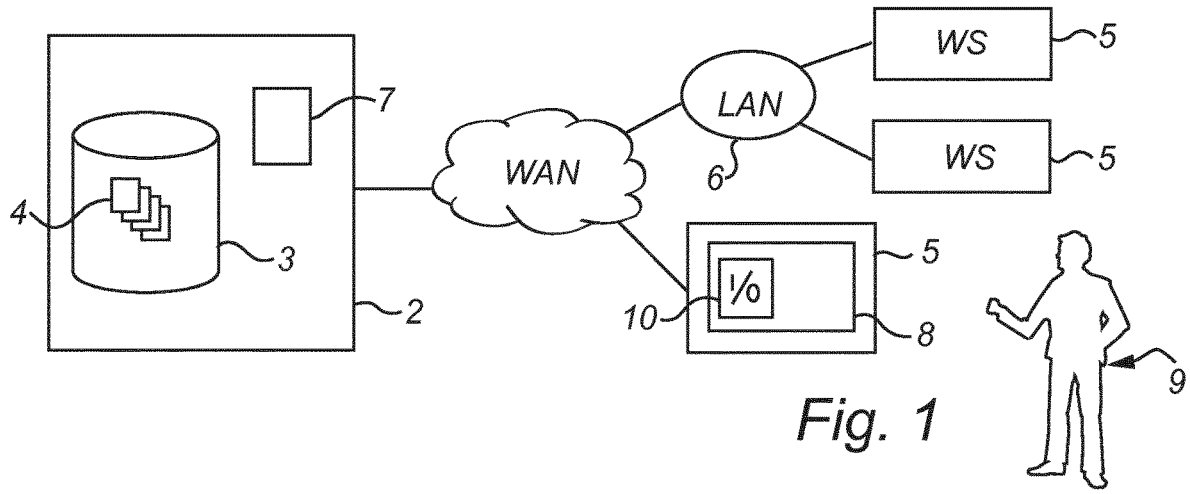
FIG. 1 is a schematic block diagram of an embodiment of the present invention.

FIG. 1 shows a network configuration of an embodiment of the present invention. The network 1 can be any wide area network such as the Internet. A database server 2 is connected to the network, and stores a database 3 including a plurality of procedure tray types 4, i.e. computer readable definitions of procedure trays.

In this context, a procedure tray is a single package including at least a set of, and preferably most of, all single use items required for a specific surgical procedure. One procedure tray may include a large number of single use items, e.g. in the order of tens of items up to a hundred items or more, ranging from protective gowns, drapes and sutures to laparoscopic and orthopedic instruments. The items are carefully organized and arranged in layers within the single package, ensuring stability and symmetry of the package, as well as accessibility of the items in a predetermined order.

A procedure tray typically includes at least protective gowns, drapes, and gloves. The gloves may be e.g. Biogel® gloves from Mölnlycke Health Care, in particular Biogel® puncture indicating double-gloves.

Additionally, a procedure tray may include some or all of the following items:

Medical dressings such as post-op dressings, wound dressings, and/or interface dressings to prevent pressure injuries, e.g. Mepilex® Border sold by Mölnlycke Health Care. Dressings are almost always used at one point or another during a surgical procedure, either to put on a suture or post-op wound or to use during the surgical procedure for pressure injury prevention. By including such dressings in the surgical tray, a more efficient procedure may be achieved.

Trocars, ports, and surgical instruments for minimal invasive surgery, such as for laparoscopy. In the case of minimal invasive surgery procedures, the need of such items may be anticipated, thereby facilitating the procedure, Single use systems for negative pressure wound treatment, typically comprising some sort of light-weight pump coupled or connectable to a dressing. Such products offer additional exudates management and can be applied to the surgical wound or closed incision.

Positioners for pressure injury prevention. These devices provide safer positioning of patients and/or cushioning of patient body parts and/or bony prominence during surgery. Examples of such positioners are inflatable sheets, pillows and wedges made of for instance foam as well as fluidized media positioners as described in e.g. US 2012/0311781.

A plurality of workstations 5 (e.g. personal computers, thin clients, or even portable devices) are also connected to the network. It is noted that the work stations 5 may be connected to the wide area network via a local area network 6, as is typical for workstations 5 within an organization such as a hospital. The system also includes a database application software 7, 8 having a server module 7, installed on the database server 2, and a set of client modules 8, one installed on each work station 5. The server module is configured to interact with the database and provide access to the data stored therein, e.g. perform read, write and query actions. The client module 8 is configured to provide a user 9 of the work station access to the database 3, and therefore includes a user interface 10. The user interface 10 is inter alia configured to provide functionality which will be discussed in further detail below.

Figure 2:
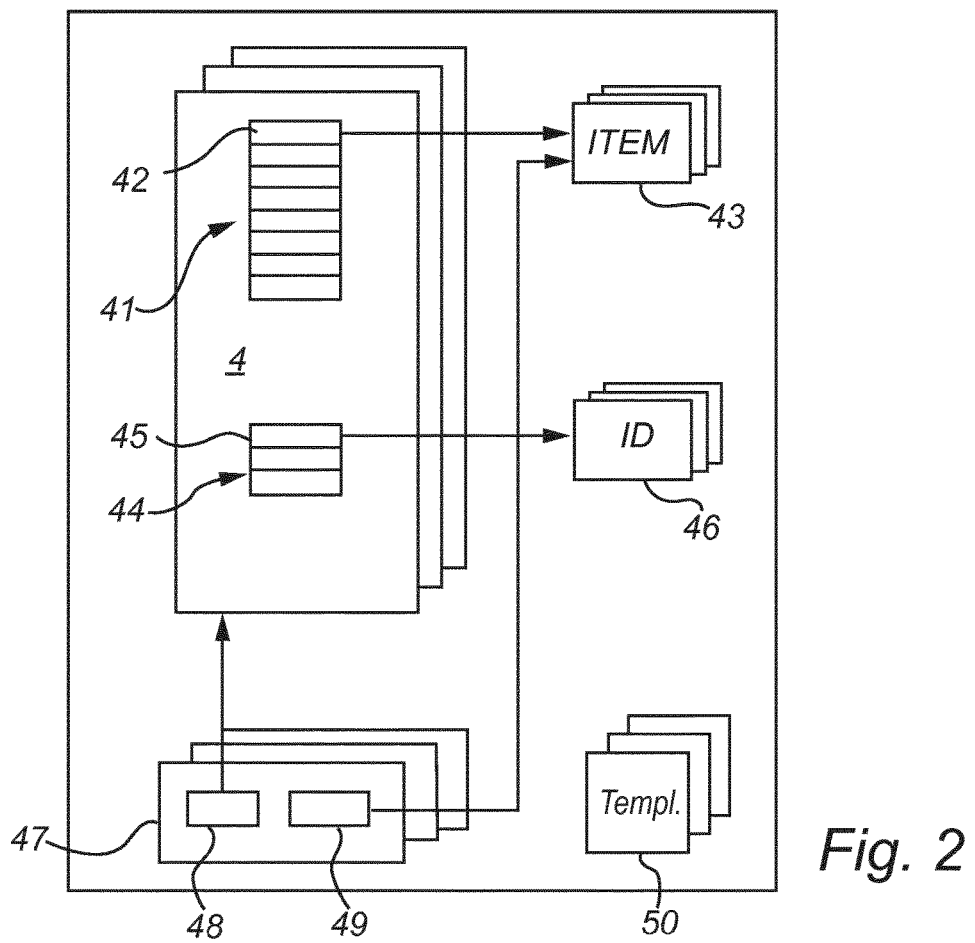
FIG. 2 is a schematic illustration of the structure of the database in FIG. 1.

FIG. 2 illustrates in more detail a possible structure of the database 3 in FIG. 1. As mentioned, the database 3 stores a plurality of procedure tray types 4. In a typical implementation, the number of different types is large, e.g. in the order of thousands. Each procedure tray type 4 includes a list 41 of items to be included in a procedure tray intended to be used in a specific surgical procedure. The list 41 is preferably a set of pointers 42 to item types 43 stored in the database. The item types may include price information. Further, each procedure tray type 4 includes a list 44 of users associated with the procedure tray type. The list 44 may also be a list of pointers 45 to user identifications 46 also stored in the database 3.

The database 3 may optionally include various purchasing information, such as volumes and discounts. Such information is typically associated with a specific purchasing entity, e.g. a specific hospital or group of hospitals. For this purpose, the database may include entries 47 for each purchasing entity, which entries include purchasing volumes 48 for each procedure tray type currently purchased by the entity. The price of a specific procedure tray type may be determined using the price information in the item types 43 and applying any discount 49 stored in the entry 47 for that specific item.

Even further, the database 2 may include a set of reference tray types, also referred to as templates, 50, each including a list of items that, according to best practice, is typically required during a specific surgical procedure. Such reference tray types may be developed based on experience and knowledge collected from practitioners. By collecting such experience, it may be ensured that the reference tray type as far as possible corresponds to the items required when a specific procedure is performed.

Figure 3:
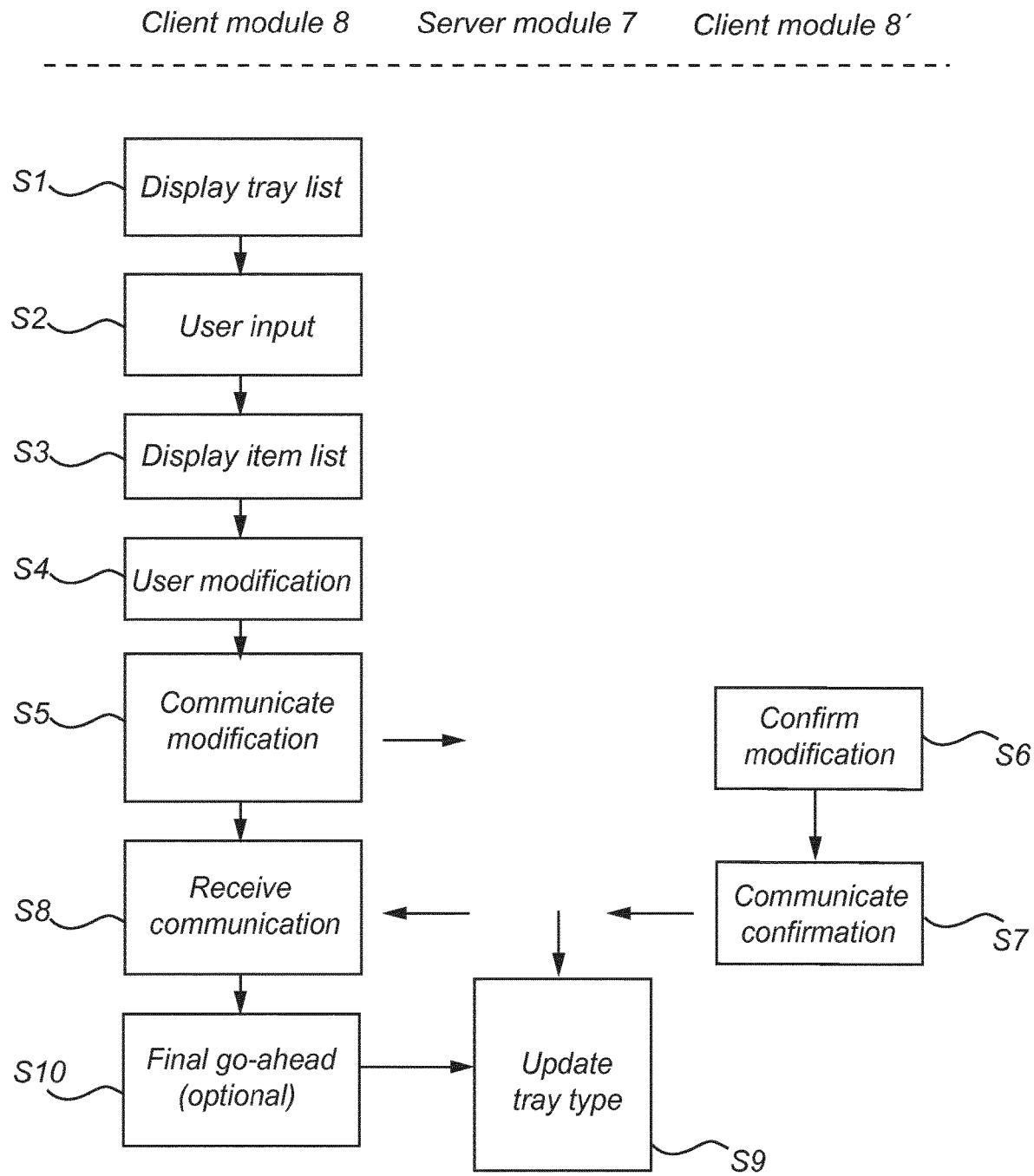
FIG. 3 is a flow chart of a method according to an embodiment of the present invention.

FIG. 3 illustrates in broad terms procedure tray management using a system according to an embodiment of the invention. The steps illustrated in FIG. 3 are assumed to succeed an initial log-on procedure, where the current user 9 is identified and procedure tray types associated with this current user are identified in the database 2.

First, in step S1, a list of the identified procedure tray types 4 are presented to the user in an appropriate format. The specific details of such presentation may be different in different applications, and may also be user dependent and possibly user controlled. The important point is that the current user is provided with an efficient overview of the procedure tray types that he or she is somehow associated with.

Then, in step S2, user input is received by the interface 10, indicating a selected one of the procedure tray types in the list. As a result, in step S3, the list 41 of items of the selected procedure tray type is displayed on the interface. Again, the details of such presentation may vary, and may be adapted to or by the user. The list should provide the current user with basic information about the contents of the selected procedure tray type, and optionally relevant purchasing information such as prices and quantities, both of the complete tray and of individual items in the tray.

Upon displaying the list of items, in step S4, the interface provides the current user with a possibility to modify the procedure tray type. Such modification may be related to adding a new sort of item, or to changing the number of items of a specific sort. Any information related to a specific item can be continuously updated to reflect the modification, and as an example, the total price of the selected procedure tray type may change as items are removed or added.

After a modification is complete (e.g. after a user input indicating that no more modifications are desired), in step S5, a proposed modified procedure tray type is electronically communicated by the client module 8 to at least some, and potentially all, users in the list 44 of users associated with the selected procedure tray type. The communication is sent over the wide area network 1, and may be of various types. In some cases an automatically generated email is sufficient, while other situations may require specifically adapted communications between client modules 8 on different workstations 5 via the server module 7.

From at least some users in the set, a confirmation is required, and such a confirmation process by another user is indicated in FIG. 3 by steps S6-S7. Step S6 is thus performed at another workstation 5' by another user 9' interacting with another client module 8'. The user interface 10' at this other workstation 5' is preferably configured to present to the user 9' any procedure tray type associated with the user for which a modification has been proposed. Such an indication may constitute the communication mentioned above, or may be in addition to a separate communication such as an email. The interface 10' may further allow the user to confirm the proposed modification e.g. by an appropriate user input (such as a mouse click or screen tap). In response to such input, the client module 8' in step S7 sends a confirmation to the server module 7.

Returning to the process at the workstation 5 and the client module 8, in step S8 the confirmation is received from the server module 7. It is noted that the receipt of confirmation from at least one user may take place at later point in time, e.g. several days after a modification was proposed. In particular, the current user may have logged off and on several times during the intermediate time period. The interface 10 is preferably configured to keep a current user informed about the status of "pending" modification, i.e. to provide, each time a current user logs on, an overview of modifications which the user has proposed, and which other users have or have not confirmed the modification.

When all required confirmations have been made, in step S9, the selected procedure tray type is updated in the database 3. Step S9 can be performed automatically by the server module 7 as soon as all required confirmations have been received. Alternatively, the server module 7 awaits a final go-ahead from the client module 8 in step S10. For example, the interface 10 may indicate to a current user when a proposed modification has been approved by all relevant user, and allow the current user to initiate a database update e.g. by an appropriate user input (such as a mouse click or screen tap).

This latter alternative is preferred in a situation where the approved modification also needs to be subject to a quotation process, which is typically the case in hospital procurement. Such a quotation process will finally verify that the estimated cost is indeed achieved, and that required volumes of individual items are in fact available at that cost.

Figure 4:
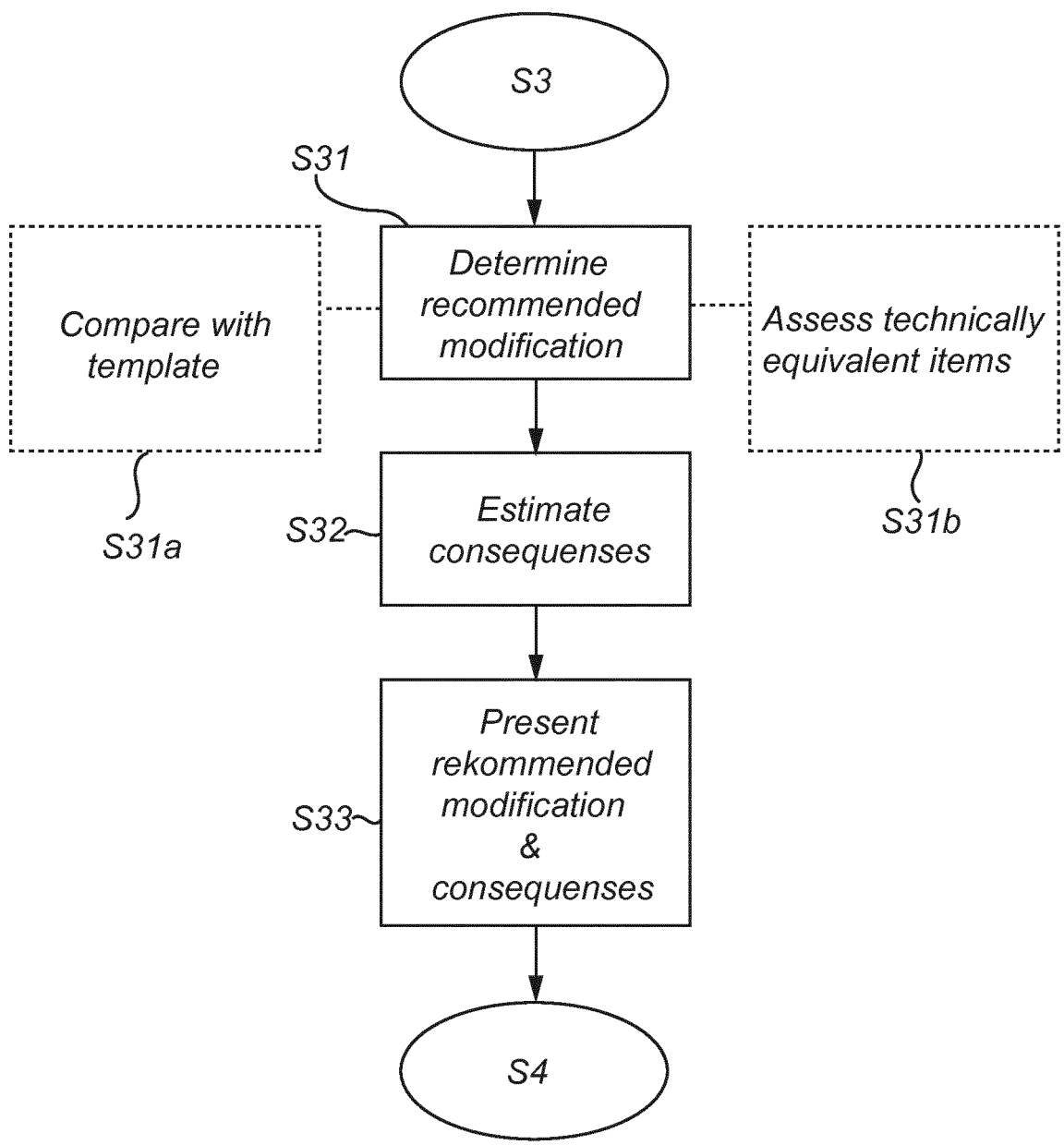
FIG. 4 shows a flow chart of a modification to the method in FIG. 3 according to a further embodiment of the invention.

FIG. 4 illustrates a further embodiment of the invention, in which additional steps have been inserted between steps S3 and S4 in FIG. 3. In step S31, a recommended modification to a particular procedure tray type is automatically determined by the database application, e.g. by the server module 7. In step S32, estimated consequences of the recommended modification are determined. For example, when a previously individually packaged item is included in a procedure tray, there may be consequences in terms of time savings (fewer packages to open), environmental impact (waste reduction in the form of less packaging material), and cost savings (the packaging material also represents a cost. When an item is substituted for a less expensive one, the consequences are primarily cost related. Finally, in step S33, the recommended modification and estimated consequences, are presented to the current user.

As indicated in FIG. 4, a recommended modification may be presented in response to the current user selecting a procedure tray type in step S3. In this case, selection of a particular procedure tray type may be the only way to receive recommendations for modifications on that tray type. However, a potentially more preferred alternative is to communicate the recommended modification to all users associated with the tray type for which the modification is proposed. In this case, the current user has typically already been presented with the recommended modification, before selecting the procedure tray type (potentially even before logging on to the system, e.g. by email). In other words, the recommended modification, if received beforehand, may influence the user's choice in step S3.

The automatically determined recommended modification may be obtained in various ways.

For example, as indicated by step S31a in FIG. 4, a particular procedure tray type may be compared with a reference tray type or template 50 stored in the database (see above). As a result of the comparison, items may be identified which are included in the reference tray type but not in the procedure tray type. Such items may be identified as recommended item additions, i.e. items that are recommended to be added to the particular procedure tray type, in order to make it comply with best practice as reflected by the reference tray type.

The recommended additions may be listed in order of increased benefit, e.g. in terms of time saving, environmental impact or cost saving.

In another example, as indicated by step S31b in FIG. 4, the database is queried to identify at least one available substitute item, i.e. an item which has equivalent technical properties as an item in the particular procedure tray type. Then, purchasing information stored in the database is used to assess the identified substitute items, in order to determine if a substitution would be beneficial to the purchasing entity. For example, it is important to ensure delivery reliability and maintained cost level. If such a beneficial substitution is found, a recommended item substitution is identified.

It is noted that the determination in step S31 and the estimation of consequences in step S32 may be performed together, and indeed the estimation of consequences such as cost may be part of the determination in step S31.

In some embodiments of the invention, users of the system are categorized into different "roles", based on their relationship with the management and procurement of procedure trays. As an example, the roles of "purchaser" and "clinical practitioner" may be defined in the system. Also a role of "administrator" may be advantageous. A purchaser will typically be responsible for ordering procedure trays to a complete hospital or group of hospital, and may thus have a large number of procedure tray types to keep track of. Cost is also a primary focus for a purchaser. A clinical practitioner (e.g. an operating room nurse) will typically be responsible for the logistics several different procedures, and thus be involved in the procedure tray types associated with these procedures. Time savings provided by the procedure trays is one of the primary concerns.

Based on their respective roles, different users may be assigned different rights (read/write) in the system, implemented by a suitable rights management system. The rights may be dynamically assigned, and may also be different within a specific role. For example, it is possible that some clinical practitioners are entrusted to see price information for specific procedure trays, while others are not.

Further, the different roles of users may influence the functionality and appearance of the system presented to a specific user. As an example, the recommendations described above may be communicated only to users having a specific role. This may be advantageous if the recommendation is not expected to be relevant for all user roles.

Further, the presentation of potential advantageous consequences of a recommended modification, as discussed above with reference to steps S32-S33, may be targeted to specific user roles. For example, estimated set-up time savings may be presented only to users in the role of clinical practitioner, while estimated costs savings may be presented only to purchasers.

A specific implementation of an embodiment of the present invention will now be described with reference to the screen shots in FIGS. 5-9.

Figure 5:
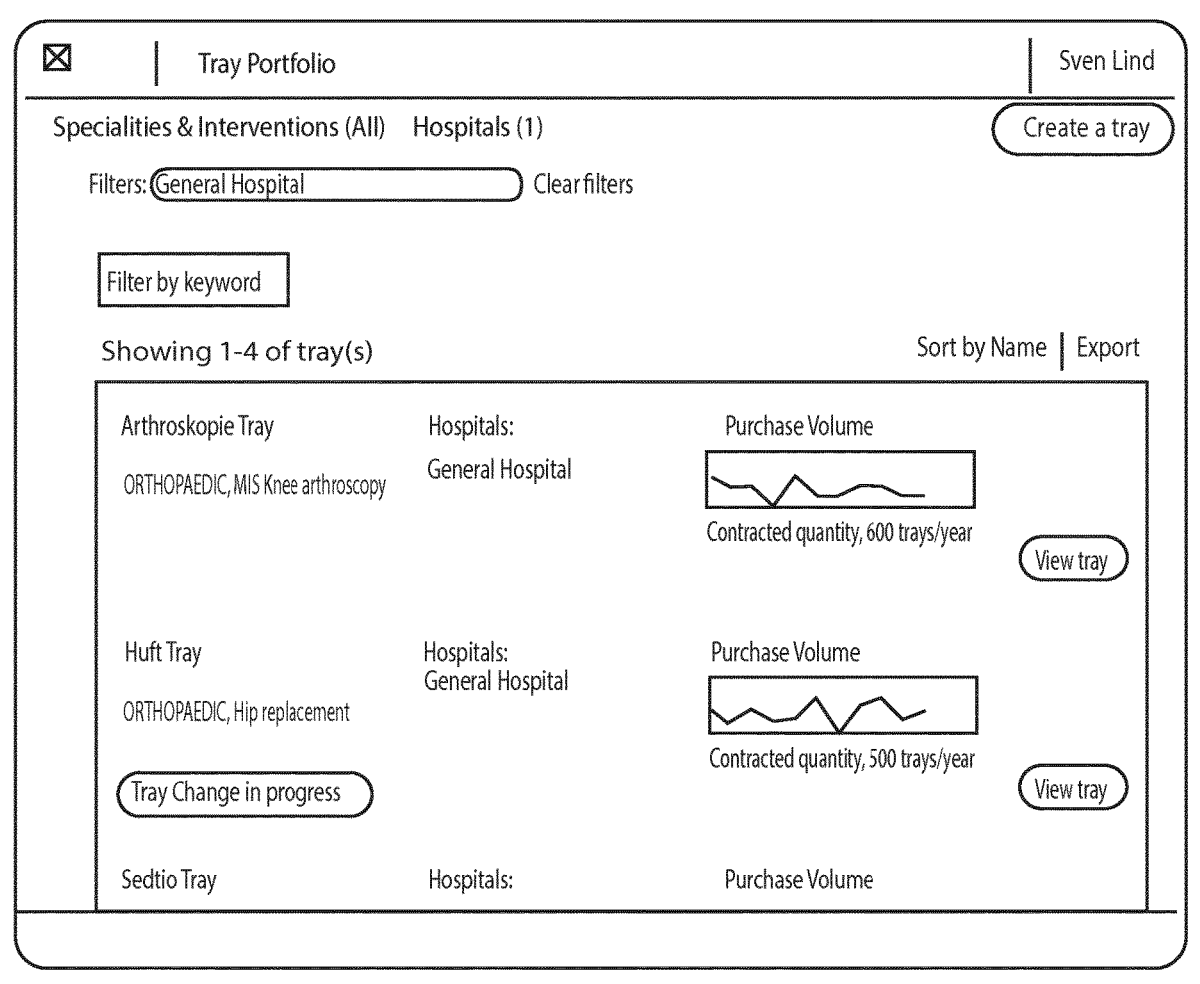

In FIG. 5, the user "Sven Lind" is logged on, and the interface presents a "tray portfolio" of this user, i.e. a list of procedure tray types that the user has access to. The interface here includes filters, which allows the user to limit the list to relevant procedure trays. In this case, the user apparently has access to procedure tray types of several hospitals, and the displayed tray portfolio has been restricted to the trays used by a specific hospital.

In the upper right corner is a button allowing the user to initiate creation of a new procedure tray from scratch, if such an option is available for the current user. The interface also includes standard functionality such as "Sort by" and "Export".

In the illustrated example, each entry in the list includes name of the tray, name of the hospital using the tray, and purchasing volume. The list may also indicate if a particular tray is currently being subject to a modification process. In the illustrated case, the second tray in the list has such an indication ("Tray Change in progress"). To the right of each entry in the list is a button labeled "View tray", with which the user may select one of the trays in the list for further review.

Figure 6:
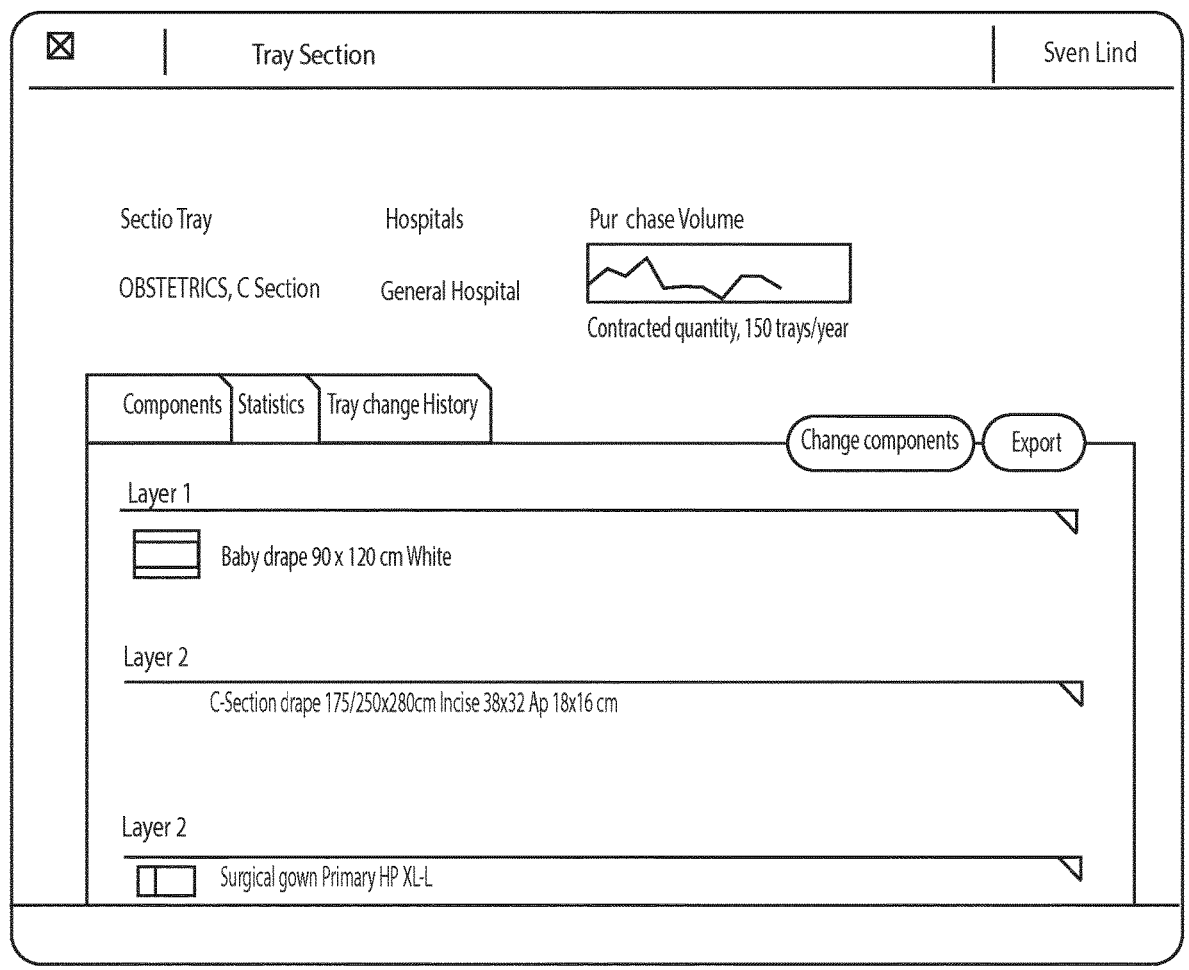

In FIG. 6, the user has selected one procedure tray in the portfolio, "Sectio Tray" and the interface now presents more details of this selected tray. In the illustrated example there are three different tabs of information; "components", "statistics", and "tray change history", and "components" is currently active. As a consequence, the interface presents a list of items of the selected procedure tray, and the quantity of each. An "Export" functionality may be useful, as the complete list of items is typically very long, and it may be difficult to get an overview on the screen.

By clicking on "change components", the user can propose a modification of the contents, e.g. increase/decrease the quantity of an item, completely remove an item, or add a new item.

The items are sorted by "layer", where "layer 1" indicates that the item is arranged at the very top of the procedure tray. The arrangement of items in layers is based primarily on the expected order of use in the procedure, but also on more physical properties, such as space efficient packaging and stability of the complete tray. The final order of items in a procedure tray is determined by a service provider responsible for packing the trays. Therefore, the actual layering of a tray may deviate from that which a user perceives as optimal, and this may be a reason for modification.

FIG. 7 is a dialogue box, provided by the interface when a modification has been proposed and is about to be communicated to other users. As discussed above, a proposed modification will be sent to a set of users associated with the procedure tray. These users appear under "mandatory reviewers". In the illustrated example, there is also an entry box allowing the current user to add additional reviewers. To the right, there is also a text entry box allowing the user to provide a comment to the reviewers. The current user initiates the communication by clicking the "send" button.

Figure 8:
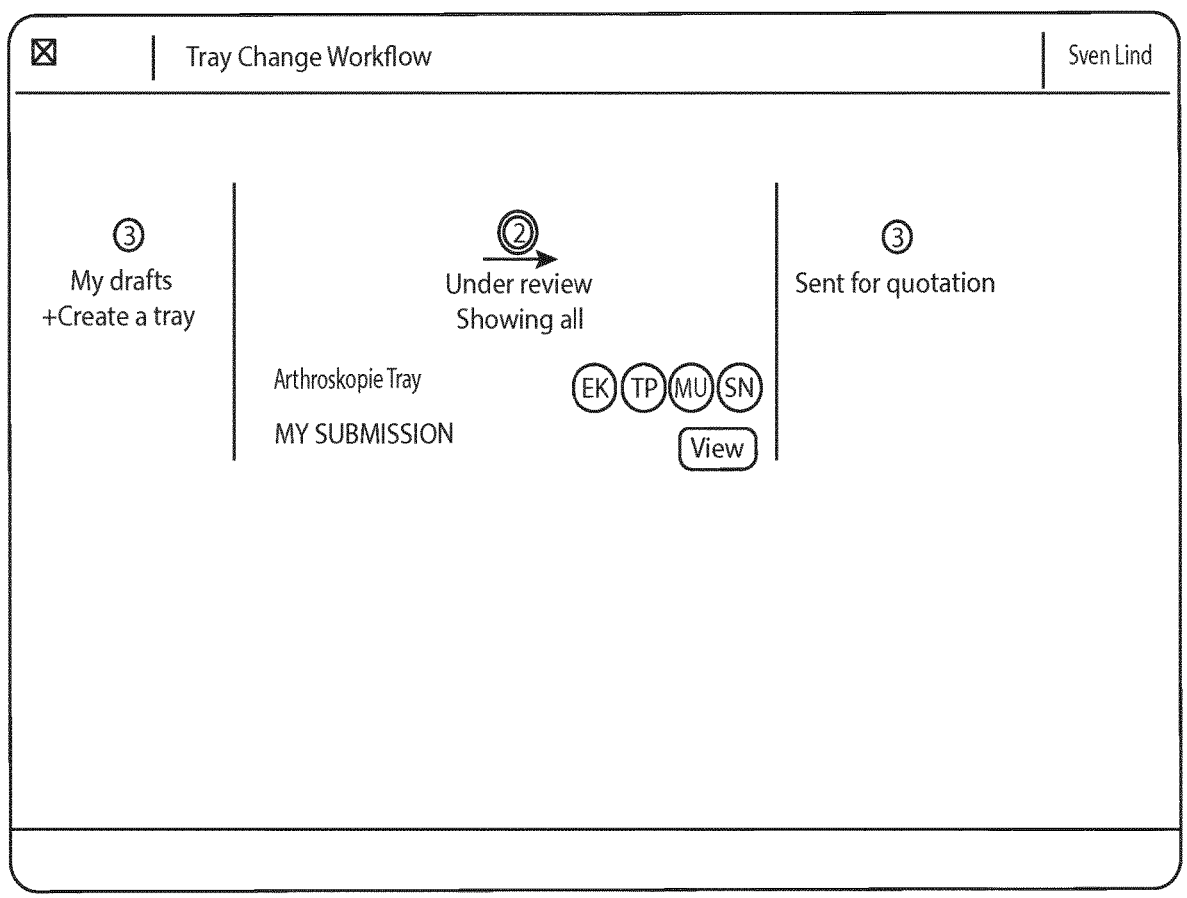

In FIG. 8, the interface presents a "tray change workflow", i.e. an overview of modifications proposed by the current user. In the left field of the screen the user can review his/hers drafts, i.e. new trays or modifications to trays which have not yet been sent for review. There are currently no such drafts for the current user. In the center field, the user can review trays that have been sent for review, and the status of the review process for these trays. There is currently one such tray listed, and in the illustrated case, circles with initials represent the required reviewers. When a reviewer has confirmed the modification, the respective circle will change color. By clicking the "view" button, the user may review the proposed modification in detail. In the illustrated example, the interface is designed for a quotation procedure as discussed above. Therefore, the interface includes a right field in which the user can review modifications that have been approved and sent for quotation.

Figure 9:
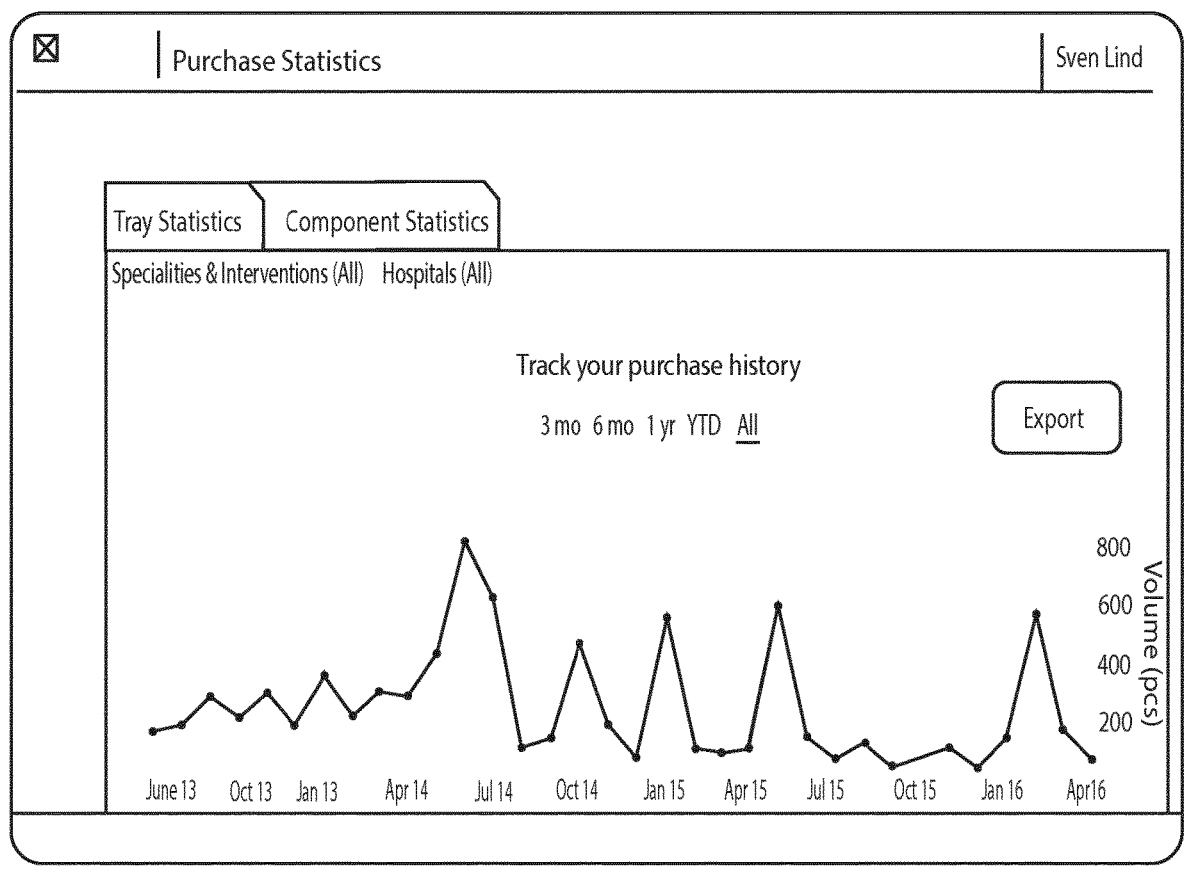

FIG. 9 is a presentation of purchasing statistics, and here includes two tabs; one for tray statistics and one for component (item) statistics. In each tab, the user can make a number of selections, here which clinical specialties to include and which hospitals to include, and the interface provides a diagram indicating the purchase of procedure trays matching the selection in a given time frame. The interface lists several available time frames, e.g. 3 months, 6 months, 1 yr, YTD, etc. The statistics may be exported to a suitable format for further analysis using an "Export" button.

The person skilled in the art realizes that the present invention by no means is limited to the preferred embodiments described above. On the contrary, many modifications and variations are possible within the scope of the appended claims. For example, the screen shots in FIGS. 5-9 include many design choices.

The invention claimed is:

1. A method comprising:
generating, based on procedure information and template information stored in a database, a user interface,
wherein the procedure information indicates a plurality of procedure tray types, wherein each procedure tray type of the plurality of procedure tray types is associated with one or more users and a list of items to be included in a procedure tray of the procedure tray type for a type of surgical procedure of a plurality of types of surgical procedures,
wherein the template information indicates, for each procedure tray type of the plurality of procedure tray types, a list of items required to perform the type of surgical procedure associated with the procedure tray type;
causing, based on the procedure information and an interaction with the user interface by a current user of the user interface, one or more procedure tray types of the plurality of procedure tray types to be displayed;
causing, based on a selection of a procedure tray type of the one or more procedure tray types by the current user, display of the list of items to be included in the selected procedure tray type;
receiving at least one modification to the list of items to be included in the selected procedure tray type;

determining, based on the selected procedure tray type, that the current user is associated with a first user role of a plurality of user roles, wherein each user role of the plurality of user roles is associated with one or more types of recommended modifications that may be displayed at the user interface and one or more types of recommended modifications that may not be displayed at the user interface;

causing, based on the at least one modification and the template information, and based on the current user being associated with the first user role, display via the user interface of at least one recommended modification to the list of items to be included in the selected procedure tray type, wherein the at least one recommended modification is associated with the one or more types of recommended modifications that may be displayed at the user interface for the first user role;

sending, to at least one other user associated with the selected procedure tray type, based on a selection of the at least one recommended modification, at least one consequence associated with the at least one recommended modification;

receiving, based on sending the at least one consequence to the at least one other user, confirmation information associated with the at least one recommended modification;

causing, based on the confirmation information, the user interface to indicate to the current user that the at least one recommended modification has been approved by the at least one other user;

receiving, via the user interface, input from the current user, wherein the input is configured to initiate a database update associated with the at least one recommended modification; and causing, based on the input from the current user, the database update to be initiated, wherein the procedure information stored in the database is updated to indicate the at least one recommended modification.

2. The method of claim 1, further comprising:

storing, in the database, purchase volume information, wherein the purchase volume information comprises aggregated purchasing volumes of individual items for a purchasing entity;

determining, based on the purchase volume information, at least one item from the list of items associated with the selected procedure tray type that may be replaced with an available substitute item based on a technical equivalency between the at least one item and the available substitute item;

comparing prices and purchase volumes associated with the at least one item and the available substitute item; and determining, based on the comparison, the at least one recommended modification to the list of items to be included in the selected procedure tray type.

3. The method of claim 1, wherein the at least one consequence associated with the at least one recommended modification comprises an estimated time saving, the method further comprising causing display of the estimated time saving.

4. The method of claim 1, wherein the at least one consequence associated with the at least one recommended modification comprises an estimated waste reduction, the method further comprising causing display of the estimated waste reduction.

5. The method of claim 1, wherein the at least one consequence is associated with an arrangement of items in layers of the selected procedure tray type, and wherein the arrangement of items in layers is associated with an expected order of use in the procedure.

6. The method of claim 1, further comprising:

determining at least two different user roles, wherein the at least two different user roles comprise at least one of: a purchaser and a clinical practitioner; and adapting, based on an indication that a current user of the user interface is associated with a user role of the at least two different user roles, functionality of the user interface.

7. The method of claim 1, further comprising:

determining at least two different user roles, wherein the at least two different user roles comprise at least one of: a purchaser and a clinical practitioner; and causing based on the current user of the user interface being associated with the first user role of the at least two different user roles, display of an estimated time saving associated with the at least one recommended modification to the list of items to be included in the selected procedure tray type.

8. The method of claim 7, wherein causing display of the estimated time saving is based on determining that the first user role of the current user is a clinical practitioner.

9. The method of claim 7, further comprising:

determining that the first user role of the current user is a purchaser; and causing based on determining that the first user role of the current user is a purchaser, display of an estimated cost reduction associated with the at least one recommended modification to the list of items to be included in the selected procedure tray type.

10. The method of claim 1, further comprising:

storing, in the database, purchase volume information, wherein the purchase volume information comprises aggregated purchasing volumes of individual items for a purchasing entity associated with the current user of the user interface;

determining, based on the purchase volume information and a request for aggregated purchasing volumes of one or more items, all items in the procedure tray types associated with the current user; and causing display of all the items in the procedure tray types associated with the current user.

11. The method of claim 1, wherein the list of items of each procedure tray type comprises at least one of: protective gowns, drapes, and gloves.

12. The method of claim 1, further comprising receiving, from a network server, the procedure information.

13. The method of claim 1, further comprising retrieving, from the database, the template information.

14. The method of claim 1, further comprising causing manufacture of the selected procedure tray type.

15. The method of claim 14, wherein the manufacture of the selected procedure tray type is based on the updated procedure information.

16. The method of claim 1, wherein the input from the current user comprises at least one of: a mouse click or a screen tap.

17. One or more computer-readable media storing processor-executable instructions that, when executed by at least one processor, cause the at least one processor to:

generate, based on procedure information and template information stored in a database, a user interface, wherein the procedure information indicates a plurality of procedure tray types, wherein each procedure tray type of the plurality of procedure tray types is associated with one or more users and a list of items to be included in a procedure tray of the procedure tray type for a type of surgical procedure of a plurality of types of surgical procedures, wherein the template information indicates, for each procedure tray type of the plurality of procedure tray types, a list of items required to perform the type of surgical procedure associated with the procedure tray type;

cause, based on the procedure information and an interaction with the user interface by a current user of the user interface, one or more procedure tray types of the plurality of procedure tray types to be displayed;

cause, based on a selection of a procedure tray type of the one or more procedure tray types by the current user, display of the list of items to be included in the selected procedure tray type;

receive at least one modification to the list of items to be included in the selected procedure tray type;

determine, based on the selected procedure tray type, that the current user is associated with a first user role of a plurality of user roles, wherein each user role of the plurality of user roles is associated with one or more types of recommended modifications that may be displayed at the user interface and one or more types of recommended modifications that may not be displayed at the user interface;

cause, based on the at least one modification and the template information, and based on the current user being associated with the first user role, display via the user interface of at least one recommended modification to the list of items to be included in the selected procedure tray type, wherein the at least one recommended modification is associated with the one or more types of recommended modifications that may be displayed at the user interface for the first user role;

send, to at least one other user associated with the selected procedure tray type, based on a selection of the at least one recommended modification, at least one consequence associated with the at least one recommended modification;

receive, based on sending the at least one consequence to the at least one other user, confirmation information associated with the at least one recommended modification;

cause, based on the confirmation information, the user interface to indicate to the current user that the at least one recommended modification has been approved by the at least one other user;

receive, via the user interface, input from the current user, wherein the input is configured to initiate a database update associated with the at least one recommended modification; and cause, based on the input from the current user, the database update to be initiated, wherein the procedure information stored in the database is updated to indicate the at least one recommended modification.

18. The one or more computer-readable media of claim 17, wherein the processor-executable instructions further cause the at least one processor to cause, based on the updated procedure information, manufacture of the selected procedure tray type.

19. The one or more computer-readable media of claim 18, wherein the processor-executable instructions that cause the at least one processor to cause manufacture of the selected procedure tray type further cause the at least one processor to cause manufacture of the selected procedure tray type based on the updated procedure information.

20. The one or more computer-readable media of claim 17, wherein the input from the current user comprises at least one of: a mouse click or a screen tap.

* * * * *